(12) United States Patent
Zhang et al.

(10) Patent No.: US 11,350,835 B2
(45) Date of Patent: Jun. 7, 2022

(54) WEARABLE DEVICE FOR REFLECTING FATIGUE LEVEL OF HUMAN BODY

(71) Applicant: JIANGSU GAREA HEALTH TECHNOLOGY CO., LTD, Suzhou (CN)

(72) Inventors: Xinjing Zhang, Suzhou (CN); Xiaodong Wang, Suzhou (CN); Jisong Hu, Suzhou (CN); Haofang Yang, Suzhou (CN)

(73) Assignee: Jiangsu Garea Health Technology Co. LTD, Suzhou (CN)

( * ) Notice: Subject to any disclaimer, the term of this patent is extended or adjusted under 35 U.S.C. 154(b) by 114 days.

(21) Appl. No.: 16/610,350

(22) PCT Filed: Jun. 10, 2019

(86) PCT No.: PCT/CN2019/090533
§ 371 (c)(1),
(2) Date: Nov. 1, 2019

(87) PCT Pub. No.: WO2020/042709
PCT Pub. Date: Mar. 5, 2020

(65) Prior Publication Data
US 2021/0161411 A1    Jun. 3, 2021

(30) Foreign Application Priority Data
Aug. 31, 2018    (CN) .......................... 201811008035.4

(51) Int. Cl.
*A61B 5/024*    (2006.01)
*A61B 5/318*    (2021.01)
(Continued)

(52) U.S. Cl.
CPC .......... *A61B 5/02405* (2013.01); *A61B 5/002* (2013.01); *A61B 5/01* (2013.01);
(Continued)

(58) Field of Classification Search
CPC ..... A61B 5/02405; A61B 5/318; A61B 5/389; A61B 5/002; A61B 5/6802; A61B 5/01;
(Continued)

(56) References Cited

U.S. PATENT DOCUMENTS

2012/0245439 A1*    9/2012    Andre .................... A61B 5/412
600/310

FOREIGN PATENT DOCUMENTS

| CN | 101584580 A | 11/2009 |
|---|---|---|
| CN | 103932683 A | 7/2014 |

(Continued)

*Primary Examiner* — Carl H Layno
*Assistant Examiner* — Aya Ziad Bakkar
(74) *Attorney, Agent, or Firm* — Vivacqua Crane PLLC (57) ABSTRACT

A wearable device for reflecting a fatigue level of a human body is disclosed. The device comprises a physiological signal acquisition module, a signal conditioning module, a parameter extraction module and a decision module. The physiological signal acquisition module is configured to acquire physiological signals of a testee. An output end of the physiological signal acquisition module is connected to an input end of the signal conditioning module. The signal conditioning module is configured to perform signal conditioning on the physiological signals. An output end of the signal conditioning module is connected to an input end of the parameter extraction module. The parameter extraction module is configured to extract time-domain and frequency-domain parameters in a specific time window. An output end of the parameter extraction module is connected to an input end of the decision module. The decision module is configured to decide a fatigue level of the testee.

6 Claims, 4 Drawing Sheets

(51) Int. Cl.
  *A61B 5/00* (2006.01)
  *A61B 5/01* (2006.01)
  *A61B 5/08* (2006.01)
  *A61B 5/389* (2021.01)
(52) U.S. Cl.
  CPC ............... *A61B 5/08* (2013.01); *A61B 5/318* (2021.01); *A61B 5/389* (2021.01); *A61B 5/6802* (2013.01); *A61B 5/725* (2013.01); *A61B 5/742* (2013.01); *A61B 2560/0214* (2013.01); *A61B 2562/0271* (2013.01)
(58) Field of Classification Search
  CPC .... A61B 2562/0271; A61B 2560/0214; A61B 5/742
  See application file for complete search history.

(56) References Cited

FOREIGN PATENT DOCUMENTS

| | | | | |
|---|---|---|---|---|
| CN | 107252313 A | * | 10/2017 | |
| CN | 107252313 A | | 10/2017 | |
| CN | 108407813 A | | 8/2018 | |
| CN | 109009028 A | | 12/2018 | |
| WO | WO-2010065067 A1 | * | 6/2010 | ............. A61B 5/413 |

* cited by examiner

FIG. 4

WEARABLE DEVICE FOR REFLECTING FATIGUE LEVEL OF HUMAN BODY

CROSS REFERENCE TO RELATED APPLICATIONS

This application is a national stage application under 35 U.S.C. 371 of PCT Application No. PCT/CN2019/090533, filed on 10 Jun. 2019, which PCT application claimed the benefit of Chinese Patent Application No. 201811008035.4, filed on 31 Aug. 2018, the entire disclosure of each of which are herein incorporated by reference.

TECHNICAL FIELD

The present disclosure relates to the technical field of human body fatigue detection, and in particular to a wearable device for reflecting a fatigue level of a human body.

BACKGROUND

The fast-pace lifestyle in the modern society leads to mental fatigue of people. If a person cannot be recovered from fatigue for a long time, it is possible to result in psychological or physical diseases.

At present, main detection means for the mental fatigue include subjective detection and objective detection. The subjective detection is mainly performed by judging subjective feelings of the testee and has large differences. The objective detection is mainly performed by acquiring physiological signals of a human body and establishing a correspondence between the physiological signals and the fatigue, so that the detection is less influenced by human factors and can be continuously performed at work and in life with accurate and reliable evaluation results.

Existing objective detection devices often extract pulse wave signals by an optical volumetric scanner and calculate the heart rate. The pulse wave signals are largely affected by the motion interference and the gap between the device and the body surface, and the signal processing is complicated. An independent sensor module is used to acquire the axillary temperature signal, so it is inconvenient. Moreover, the accuracy of measurement and decision is limited.

SUMMARY

The technical problems to be solved by the present disclosure are as follows: the indirect heart rate calculating method has high complexity and large signal interference; it is inconvenient to acquire the body temperature; the accuracy of measurement and decision is limited; and the like.

To solve the technical problems, the technical solutions adopted by the present disclosure are as follows:

A wearable device for reflecting a fatigue level of a human body is provided, the device includes a physiological signal acquisition module, a signal conditioning module, a parameter extraction module and a decision module; wherein the physiological signal acquisition module is configured to acquire physiological signals of a testee; an output end of the physiological signal acquisition module is connected to an input end of the signal conditioning module; the signal conditioning module is configured to perform signal conditioning on the physiological signals; an output end of the signal conditioning module is connected to an input end of the parameter extraction module; the parameter extraction module is configured to extract time-domain and frequency-domain parameters in a specific time window; an output end of the parameter extraction module is connected to an input end of the decision module; and, the decision module is configured to decide a fatigue level of the testee.

Further, the physiological signal acquisition module includes electrocardio-electrodes and a body temperature acquisition module, which are configured to acquire electrocardio-electrode physiological signals and body temperature physiological signals, respectively.

Further, the body temperature acquisition module includes a temperature sensor and a compensation module, wherein the temperature sensor comes into contact with the skin of the testee, and is configured to detect a change in body temperature of the testee and converting the body temperature of the testee into a standard body temperature through the compensation module.

Further, the signal conditioning module includes a filtering circuit.

Further, the electrocardio-electrodes include two or more electrocardio-electrodes.

Further, the device further includes a wireless communication module, a local storage module, a display and feedback module and a power supply module.

A method for deciding a fatigue level of a human body based on the wearable device for reflecting a fatigue level of a human body is provided, the method includes the following steps:

S1: acquiring physiological signals;

S2: processing, by a signal conditioning module, the detected data to obtain an electrocardiographic signal, a respiratory signal, a myoelectric signal and a standard body temperature, respectively;

S3: further extracting, by a parameter extraction module, corresponding feature values according to the electrocardiographic signal, the respiratory signal, the myoelectric signal and the standard body temperature obtained in the step S2; and S4: setting, by a decision module and according to the change trend of the body temperature, an upper threshold limit and a lower threshold limit for the electrocardiographic signal, the respiratory signal and the myoelectric signal, to decide whether it is normal or abnormal, and performing logical combining to obtain a fatigue level model for further deciding the fatigue level.

Further, the step S2 further includes the following steps:

S21: performing, by the signal conditioning module, signal conditioning on signals acquired by electrocardio-electrodes, and extracting an electrocardiographic signal, a respiratory signal and a myoelectric signal in the electrocardio-electrode signals by different frequency band filtering; and S22: performing temperature compensation on a body temperature signal to obtain a standard body temperature.

Further, the step S3 further includes the following steps:

S31: extracting, from the electrocardiographic signal, feature values of heart rate variability;

S32: extracting, from the respiratory signal, feature values (such as a maximum value and a minimum value) of the respiratory frequency;

S33: extracting, from the myoelectric signal, feature values such as a median frequency and an average frequency; and S34: extracting, from the standard body temperature signal, feature values (such as a maximum value, a minimum value, a mean value and a standard deviation) of the body temperature.

Further, the step S22 specifically includes that: determining a standard body temperature by weighted average values of shell temperatures at a plurality of test points, or determining a standard body temperature by compensating a shell temperature of a test point.

The wearable device for reflecting a fatigue level of a human body provided by the present disclosure has the following beneficial effects: 1) by directly acquiring an electrocardio signal, the complexity of hardware and software analysis of the device is reduced; 2) by integrating a body temperature sensor into the device, it is convenient to wear, and by providing a multi-parameter portable wearable mode, a user can realize real-time monitoring freely; and, 3) by performing a logical combining operation or normalized logical combining operation by using multiple parameters such as an electrocardio signal, a myoelectric signal, a respiratory signal and a body temperature signal, the scientificity and accuracy of decision are improved.

DETAILED DESCRIPTION

The present disclosure will be described in more detail with reference to the accompanying drawings in which the preferred embodiments of the present disclosure are shown. It should be understood that those skilled in the art can still achieve the beneficial effects of the present disclosure by making modifications to the present disclosure described herein. Therefore, the following description should be regarded as the broad understanding of those skilled in the art, rather than limiting the present disclosure.

For clarity, not all features of the practical embodiments will be described. In the following description, well-known functions and structures will not be described in detail since the functions and structures will obscure the present disclosure due to unnecessary details. It should be recognized that in the development of any practical embodiment, a large amount of implementation details must be made to achieve the developer's specific goal.

To make the objectives and features of the present disclosure more comprehensible, the specific implementations will be further described below with reference to the accompanying drawings. It is to be noted that the accompanying drawings are drawn in a very simplified form and at a non-accurate ratio, and are merely used for conveniently and clearly assisting in explaining the objectives of the embodiments of the present disclosure.

Figure 1:
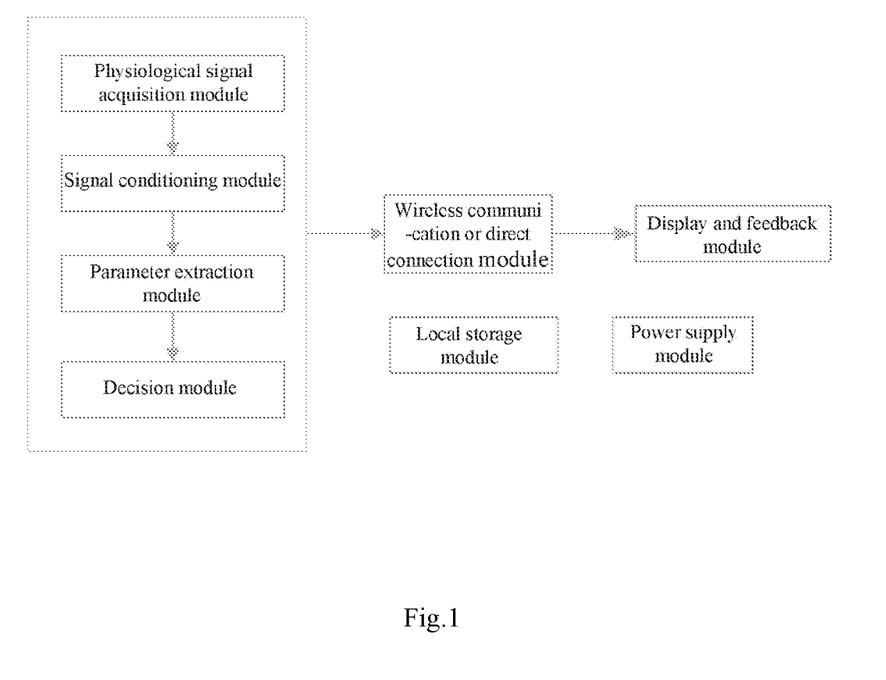
FIG. 1 is a schematic diagram of an overall structure of a wearable device for reflecting a fatigue level of a human body according to the present disclosure.

The present embodiment provides a wearable device for reflecting a fatigue level of a human body. As shown in FIG. 1, the device includes a physiological signal acquisition module, a signal conditioning module, a parameter extraction module, a decision module, a wireless communication module, a local storage module, a display and feedback module and a power supply module. Wherein, the physiological signal acquisition module is configured to acquire physiological signals of a testee. An output end of the physiological signal acquisition module is connected to an input end of the signal conditioning module. The signal conditioning module is configured to perform signal conditioning on the physiological signals. An output end of the signal conditioning module is connected to an input end of the parameter extraction module. The parameter extraction module is configured to extract time-domain and frequency-domain parameters in a specific time window. An output end of the parameter extraction module is connected to an input end of the decision module. The decision module is configured to decide a fatigue level of the testee.

The main modules of the wearable device for reflecting a fatigue level of a human body provided by the present application will be described below.

Physiological Signal Acquisition Module

The physiological signal acquisition module includes electrocardio-electrodes and a body temperature acquisition module, which are configured to acquire electrocardio-electrode physiological signals and body temperature physiological signals, respectively.

Wherein, the electrocardio-electrodes include two or more electrocardio-electrodes. The electrocardio-electrodes may be preferably arranged on a heart rate monitor. It is also possible to form a wearable garment such as a tight measurement vest by hybrid weaving metal wires and common fabric. The two or more electrodes are at least tightly fixed at and come into contact with a position above the heart on the left chest of the testee, so as to acquire an electrocardio-electrode physiological signal of the testee. The above-mentioned electrocardio-electrode physiological signal can be separated into three signals, i.e., an electrocardio signal, a respiratory signal and a myoelectric signal, by post-processing. That is, the electrocardio-electrode physiological signal includes an electrocardio signal, a respiratory signal and a myoelectric signal.

Preferably, if the electrodes are arranged on the heart rate monitor, the heart rate monitor may be in communication with other components via a wireless communication connection. The specific connection way may be a local network, Bluetooth or Zigbee. If the electrodes are formed by a hybrid weaving method, the communication with other components can also be realized by an external circuit that is formed by weaving metal wires in the garment.

The body temperature acquisition module includes a temperature sensor and a compensation module. Wherein, the temperature sensor is exposed to the surface of the wearable device and comes into contact with the skin of the testee. It is configured to detect the change in body temperature of the testee. Preferably, the temperature sensor may be mounted on the heart rate monitor or the tight garment together with the electrocardio-electrodes, so that the body temperature signal on the testee can be obtained more accurately. A shell temperature signal is acquired by the temperature senor and then converted into a standard body temperature by the compensation module so as to obtain a real body temperature signal of the human body.

Specifically, there may be a plurality of (preferably 4) temperature sensors. The plurality of temperature sensors can be arranged at a plurality of parts of the body of the testee, for example at four positions of the head, the chest, the upper arm and the axilla. The standard body temperature is equal to (i1T1+i2T2+i3T3+ . . . +inTn); wherein n is the number of temperature measurement points, T1 to Tn are shell temperatures at the measurement points, i1 to in are parameters corresponding to the temperature points, and i1+i2+i3+ . . . +in=1. Before detection, the detection positions of the shell temperature is systematically set, a weighed value of the body temperatures at different parts is obtained by reading a corresponding data table in a local storage module through the compensation module, and a combination of a set of parameters is further obtained through the weighted value.

Alternatively, it is also possible to provide one temperature sensor. The temperature sensor may be selectively arranged at a part of the body of the testee, for example, on the head, chest, upper arm, axilla or the like. By measuring the shell temperature T at the above mentioned positions and by reading a correction value in a corresponding data table in the local storage module through the compensation module, the shell temperature at the specific position is converted into a standard body temperature. The standard body temperature is equal to T+Tc, wherein Tc is the correction value. Before detection, the detection position of the shell temperature is systematically set, a correction value corresponding to the measured part is obtained by reading a corresponding data table in the local storage module through the compensation module, and the shell temperature and the correction value are fitted to obtain a standard body temperature.

The electrocardio-electrode physiological signals and body temperature physiological signals acquired by the physiological signal acquisition module are transmitted to the local storage module for storage through a wireless or wired communication device.

Signal Conditioning Module

The signal conditioning module perform frequency-division detection on the physiological signals through a filter circuit, so that the signals from the electrodes are conditioned to obtain an electrocardio signal, a respiratory signal and a myoelectric signal, respectively.

Figure 2:
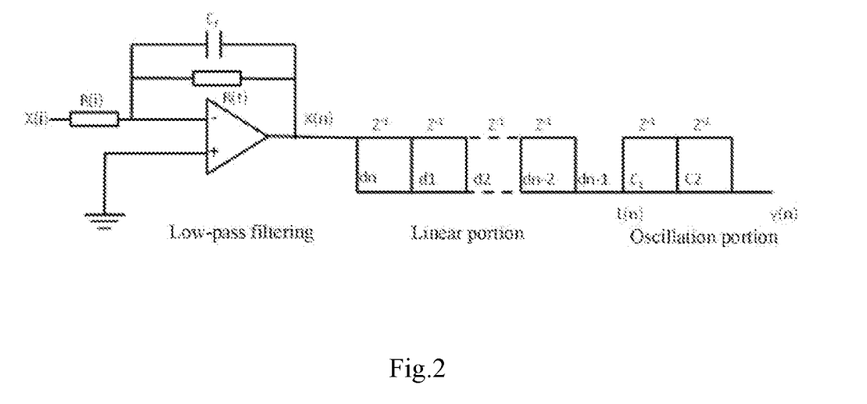
FIG. 2 is a diagram of a filter circuit in a signal conditioning module.

The signal conditioning module includes a filter circuit, as shown in FIG. 2. The signal conditioning module includes a low-pass filtering portion, a linear portion and a resonance portion. The low-pass filtering portion employs a first-order low-pass filtering mode, and the signal is low-pass filtered by an amplifier. Better attenuation performance can be realized due to the use of the amplifier instead of inductive filtering. The signal processed by the low-pass filtering portion is further subjected to frequency-divisional filtering by the linear portion and the resonance portion.

By realizing the filtering by this structure, the filter is allowed to have strict linear phase characteristics. On the other hand, since the filter coefficient is an integral power, the conventional floating-point multiplication can be replaced with a simple shift operation, so that the operation efficiency is very high. Moreover, the low-pass filter can be easily extended to a high-pass, band-pass or band-stop simple integral coefficient filter.

During the signal filtering process, due to the characteristics of different signals, the signals are extracted by band-pass filtering at different frequency bands. Specifically, since the frequency of respiratory signal is lower than 0.5 Hz, the respiratory signal is extracted by a first band-pass filtering; since the main wave frequency of QRS in the electrocardio signal is about 5 to 15 Hz, the electrocardio signal is extracted by a second band-pass filtering; and, since the energy of the myoelectric signal is mainly centralized at 20 to 150 Hz, 50 Hz power frequency interference is filtered and thus removed by a third band-stop filtering, and the myoelectric signal is extracted by a fourth band-pass filtering. The above mentioned first, second and fourth band-pass frequencies correspond to the corresponding signal frequencies, and the third band-stop frequency is 50 Hz.

Preferably, in order to reduce the storage space, signal down-sampling may be considered.

Parameter Extraction Module

The parameter extraction module is configured to perform parameter extraction and analysis on the signals subjected to the signal conditioning.

For the electrocardio signal, the parameter extraction module performs heart rate variability analysis to extract time-domain and frequency-domain parameters in a certain time window. Wherein, the frequency-domain parameter LF/HF can be used to evaluate the balance of sympathetic and parasympathetic nerves. The RMSSD is the root mean square of a difference between adjacent sinus heartbeats in the time window. The time domain in the time window is preferably 5 min.

For the respiratory signal, the maximum value, minimum value, mean value and standard deviation of the respiratory frequency in a certain time widow are extracted, and a normalized value of parameters within 5 consecutive mins is calculated by a z-Score method. The normalized value can reduce the individual difference to a certain extent, and highlight the variability. The time window is preferably 30 s. The respiratory signal can also be extracted by the low-frequency component of the heart rate variability index.

The power spectrum of the myoelectric signal is analyzed to extract a median frequency and an average frequency.

For the above mentioned body temperature signal, the maximum value, minimum value, mean value and standard deviation of the body temperature signal in a certain time window (preferably 30 s) are extracted, and a normalized value of parameters within 5 consecutive mins is calculated by a z-Score method. The normalized value can reduce individual difference to a certain extent, and highlight the variability. For the above mentioned body temperature signal represented by the standard body temperature, fitting a function T'[t] between the standard body temperature and the changes in time.

Decision Module

The decision module sets, according to the change trend of the body temperature signal, an adaptive upper threshold limit and a lower threshold limit (i.e., TH and TL, respectively) for the electrocardio signal, the myoelectric signal and the respiratory signal. When a parameter feature value is lower than TH and higher than TL, a state variable state[i] of the parameter is set as logic 1. At this time, the parameter is in a normal state. When the parameter value is higher than TH or is lower than TL, i.e., in an abnormal state, state[i] is set as 0, wherein i is the serial number of the corresponding parameter.

Specifically, the method for setting the threshold according to the change trend of the body temperature signal is as follows.

The change trend of the body temperature signal is divided into the following three functions, wherein CT[K] represents a function of a change trend of the standard body temperature signal over time, and T'[i] represents the derivative of the standard body temperature-time function with respect to the time in a specific time window.

$$CT[K] = \begin{cases} \dfrac{T'[i+1] - T'[i]}{|T'[i+1] - T'[i]|} > 0, \\ \dfrac{T'[i+1] - T'[i]}{|T'[i+1] - T'[i]|} < 0, \\ T'[i+1] - T'[i] = 0, \end{cases}$$

The threshold for each parameter is determined from a data table according to different functions. The data table is stored in the local storage module, and the decision module can read the data table in the storage module for purpose of calculation. The data table is shown below:

|  | Function | | | | | |
|---|---|---|---|---|---|---|
|  | CT[K] > 0 | | CT[K] < 0 | | CT[K] = 0 | |
| Threshold | TH | LH | TH | LH | TH | LH |
| LF/HF | 70% | 15% | 63% | 20% | 80% | 35% |
| RMSSD | 30 | 11 | 45 | 20 | 45 | 15 |
| Maximum value of the respiratory frequency (times/min) | 60 | 36 | 75 | 24 | 65 | 20 |
| Minimum value of the respiratory frequency (times/min) | 35 | 10 | 27 | 18 | 30 | 12 |
| Mean value of the respiratory frequency (times/min) | 44 | 17 | 50 | 27 | 45 | 20 |
| Standard deviation of the respiratory frequency (times/min) | 10 | 2 | 7 | 2 | 10 | 3 |
| Median frequency of the myoelectric signal (Hz) | 350 | 100 | 300 | 100 | 350 | 100 |
| Average frequency of the myoelectric signal (Hz) | 400 | 140 | 480 | 100 | 480 | 150 |

The data in the table is determined by clinical analysis data, and the thresholds in the table can be corrected according to different clinical analysis data in practical applications. The table is shown as a preferred embodiment.

When a parameter feature value is lower than TH and higher than TL, a state variable state[i] of the parameter is set as logic 1. At this time, the parameter is in a normal state. When the parameter value is higher than TH or is lower than TL, i.e., in an abnormal state, state[i] is set as 0, wherein i is the serial number of the corresponding parameter.

Therefore, after the electrocardio signal, the myoelectric signal and the respiratory signal are subjected to threshold comparisons, the respective state function is as follows:

State electrocardio[i]={state LF/HF[i], state RMSSD[i]},
State myoelectric[i]={state median frequency[i], state average frequency[i]};
State respiratory[i]={state maximum value[i], state minimum value[i], state mean value[i], state standard deviation [i]}, wherein each state parameter represents a corresponding state 0 or 1.

A logical operation is performed on the above mentioned states, for example AND of all states. The logical operation includes at least one of AND, OR, NOT, XOR and XNOR. Models corresponding to different fatigue levels can be obtained by different logical operations, so that the fatigue level of the testee is decided. As a preferred embodiment, the logical operation may be: (State electrocardio[i] & State myoelectric[i])|(State electrocardio[i] & State respiratory[i]) |(State myoelectric [i] & State respiratory[i])|(State electrocardio[i] & State myoelectric[i] & State respiratory[i]), wherein "&" represents "AND", "|" represents "OR", and "( )" represents the highest priority.

As an alternative embodiment, each the state function state[i] can be normalized in advance, and then the logical calculation is performed, so that the accuracy of the logical operation model is improved. The normalization may be performed by a normalization model known in the art.

A state logical function of each parameter can be obtained by the state logical operation. The function is a model corresponding to a different fatigue level. The state logical function can be compared and fitted with a plurality of fatigue level models stored in advance in the local storage module; in combination with the body temperature signal parameter, the fatigue level model corresponding to the state logical function can be decided, and the fatigue level is thus determined.

Display and Feedback Module

The display and feedback module includes an LED lamp static reminder, a motor dynamic reminder, or automatically communicates with a mobile phone when a fatigue event occurs, and intelligently remind the user by SMS or APP notification.

Wireless Communication Module

The wireless communication module enables the connection between the device and an intelligent terminal, and displays the data or result on a mobile phone or a PC or transmits the data or result to a cloud platform.

Local Storage Module

The local storage module is configured to locally and continuously store the acquired original data, the data subjected to the signal conditioning, state parameters or the like. The local storage module also pre-stores data table compensated by the standard body temperature, the threshold data table of the parameters or the like for further uses in calculation of the subsequent data processing.

Power Supply Module

The power supply module supplies power to the wearable device to meet the requirements of the device for independent operation. The power supply charging way includes wireless charging, USB charging or other direct charging ways.

A sleep monitoring method based on the wearable device for improving the accuracy of sleep monitoring will be described below with reference to FIG. 3.

Figure 3:
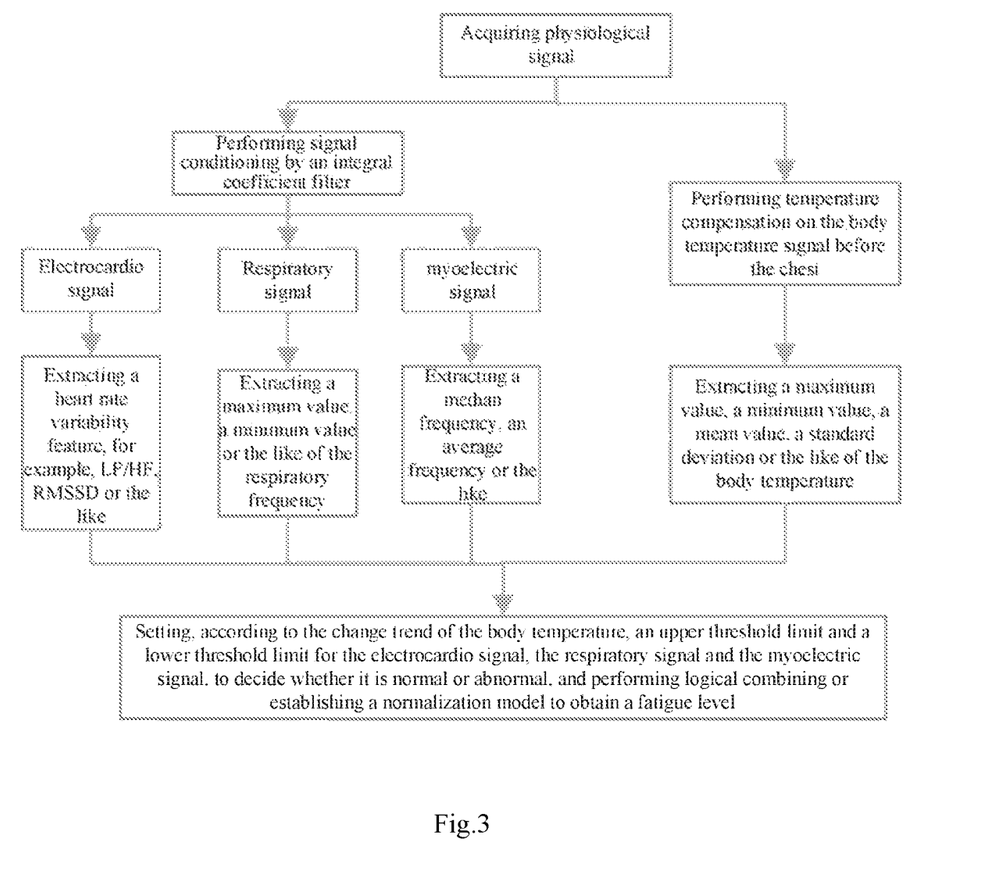
FIG. 3 is a flowchart of a detection method based on the wearable device for reflecting a fatigue level of a human body according to the present disclosure.

As shown in FIG. 3, the sleep monitoring method includes the following steps:

S1: Physiological signals are acquired.

Wherein, electrocardio-electrode physiological signals and body temperature physiological signals of a testee are acquired by electrocardio-electrodes and a temperature sensor in a signal acquisition module, respectively.

S2: The detected data is processed by a signal conditioning module to obtain an electrocardio signal, a respiratory signal, a myoelectric signal and a standard body temperature, respectively.

The step S2 further includes the following steps:

S21: Signal conditioning is performed, by the signal conditioning module, on signals acquired by electrocardio-eletrodes, and an electrocardio signal, a respiratory signal and a myoelectric signal in the electrocardio-electrode signals are extracted by different frequency band filtering.

Specifically, the signals are extracted by the signal conditioning module according to the frequency band characteristics of different signals using band-pass filtering at different frequency bands. Since the frequency of the respiratory signal is lower than 0.5 Hz, the main wave frequency of QRS in the electrocardio signal is about 5 to 15 Hz and the energy of the myoelectric signal is mainly centralized at 20 to 150 Hz, the respiratory signal is extracted by a first low-pass filtering, the electrocardio signal is extracted by a second band-pass filtering, the 50 Hz power frequency interference is filtered by a third band-stop filtering, and the myoelectric signal is extracted by a fourth band-pass filtering. Preferably, in order to reduce the storage space, signal downsampling may be considered.

S22: Temperature compensation is performed on the body temperature signal to obtain a standard body temperature.

Figure 4:
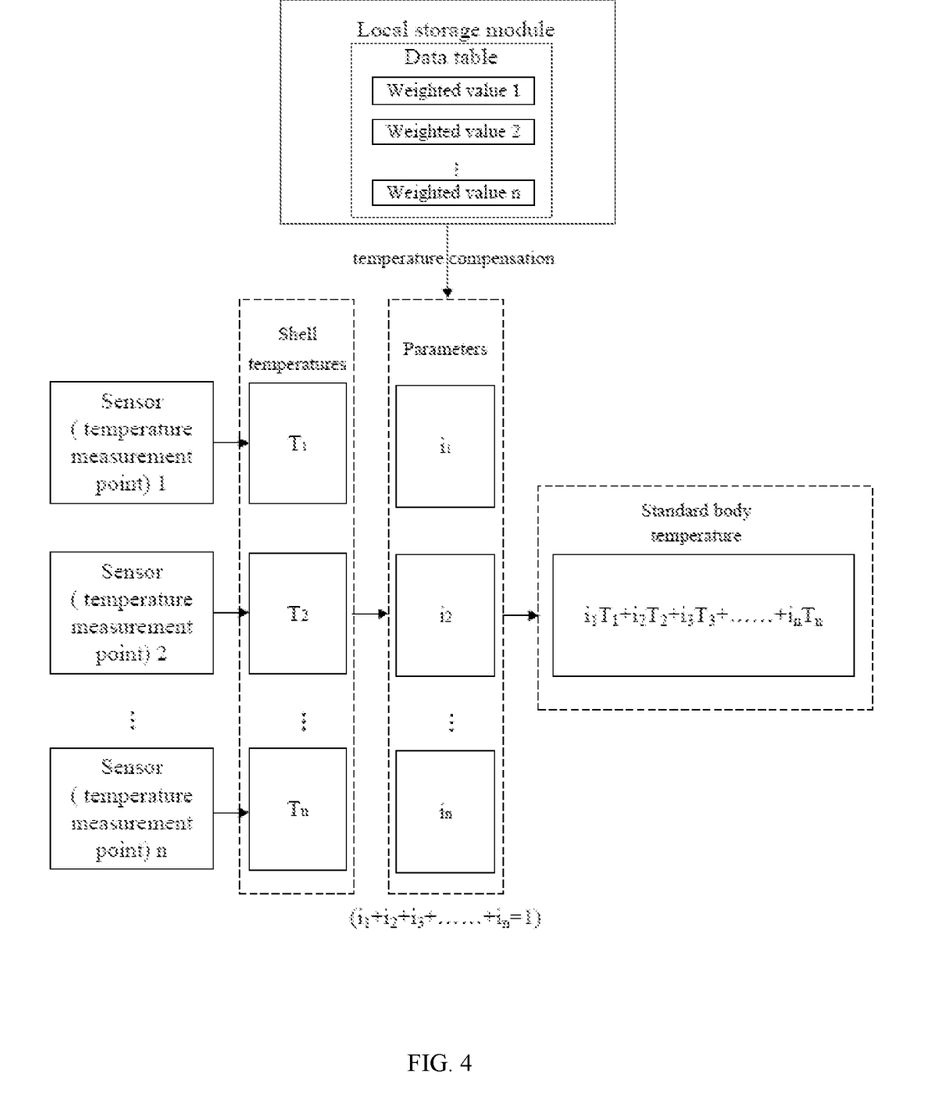
FIG. 4 is a functional diagram for the calculation of standard body temperature and weight values.

There may be a plurality of (preferably 4) temperature sensors. The plurality of temperature sensors can be arranged at a plurality of parts of the body of the testee, for example at four positions, such as the head, the chest, the upper arm and the axilla. The standard body temperature is equal to (i1T1+i2T2+i3T3+ . . . +inTn), wherein n is the number of temperature measurement points, i1 to in are parameters corresponding to the temperature points, and i1+i2+i3+ . . . +in=1. Before detection, the detection position of the shell temperature is systematically set, a weighed value of the body temperatures at different parts is obtained by reading a corresponding data table in a local storage module through the compensation module, and a combination of a set of parameters is further obtained through the weighted value.

Alternatively, it is also possible to provide one temperature sensor. The temperature sensor may be selectively arranged at a part of the body of the testee, for example, on the head, chest, upper arm, axilla or the like. By measuring the shell temperature T at one of the above mentioned positions and by reading a correction value in a corresponding data table in the local storage module through the compensation module, the shell temperature at the specific position is converted into a standard body temperature. The standard body temperature is equal to T+Tc, wherein Tc is the correction value. Before detection, the detection position of the shell temperature is systematically set, a correction value corresponding to the measured part is obtained by reading a corresponding data table in the local storage module through the compensation module, and the shell temperature and the correction value are fitted to obtain a standard body temperature.

S3: Corresponding feature values are further extracted by a parameter extraction module according to the electrocardio signal, the respiratory signal, the myoelectric signal, the standard body temperature and the motion data obtained in the step S2.

Specifically, the step S3 further includes the following steps:

S31: Feature values of heart rate variability (e.g., LF/HF, RMSSD or the like) are extracted from the electrocardio signal;

S32: Feature values (such as a maximum value and a minimum value) of the respiratory frequency are extracted from the respiratory signal;

S33: Feature values such as a median frequency and an average frequency are extracted from the myoelectric signal;

S34: Feature values (such as a maximum value, a minimum value, a mean value and a standard deviation) of the body temperature are extracted from the standard body temperature signal.

S4: The upper threshold limit and the lower threshold limit for the electrocardio signal, the respiratory signal and the myoelectric signal are set by a decision module according to the change trend of the body temperature to decide whether it is normal or abnormal, and logical combining is performed or a normalization model is established to obtain a fatigue level.

Specifically, the method for setting the threshold according to the change trend of the body temperature signal is as follows.

The change trend of the body temperature signal is divided into the following three functions, wherein CT[K] represents a function of a change trend of the standard body temperature signal over time, and T'[i] represents the derivative of the standard body temperature-time function with respect to the time in a specific time window.

$$CT[K] = \begin{cases} \dfrac{T'[i+1] - T'[i]}{|T'[i+1] - T'[i]|} > 0, \\ \dfrac{T'[i+1] - T'[i]}{|T'[i+1] - T'[i]|} < 0, \\ T'[i+1] - T'[i] = 0, \end{cases}$$

The threshold for each parameter is determined from a data table according to different functions. The data table is stored in the local storage module. The data table is shown below:

| | Function | | | | | |
|---|---|---|---|---|---|---|
| | CT[K] > 0 | | CT[K] < 0 | | CT[K] = 0 | |
| Threshold | TH | LH | TH | LH | TH | LH |
| LF/HF | 70% | 15% | 63% | 20% | 80% | 35% |
| RMSSD | 30 | 11 | 45 | 20 | 45 | 15 |
| Maximum value of the respiratory frequency (times/min) | 60 | 36 | 75 | 24 | 65 | 20 |
| Minimum value of the respiratory frequency (times/min) | 35 | 10 | 27 | 18 | 30 | 12 |
| Mean value of the respiratory frequency (times/min) | 44 | 17 | 50 | 27 | 45 | 20 |
| Standard deviation of the respiratory frequency (times/min) | 10 | 2 | 7 | 2 | 10 | 3 |
| Median frequency of the myoelectric signal (Hz) | 350 | 100 | 300 | 100 | 350 | 100 |
| Average frequency of the myoelectric signal (Hz) | 400 | 140 | 480 | 100 | 480 | 150 |

The data in the table is determined by clinical analysis data, and the thresholds in the table can be corrected according to different clinical analysis data in practical applications. The table is shown as a preferred embodiment.

When a parameter feature value is lower than TH and higher than TL, a state variable state[i] of the parameter is set as logic 1. At this time, the parameter is in a normal state. When the parameter value is higher than TH or is lower than TL, i.e., in an abnormal state, state[i] is set as 0, wherein i is the serial number of the corresponding parameter.

Therefore, after the electrocardio signal, the myoelectric signal and the respiratory signal are subjected to threshold comparison, the respective state function is as follows:

State electrocardio[i]={state LF/HF[i], state RMSSD[i]};

State myoelectric[i]={state median frequency[i], state average frequency[i]};

State respiratory[i]={state maximum value[i], state minimum value[i], state mean value[i], state standard deviation [i]}, wherein each the state parameter represents a corresponding state 0 or 1.

A logical operation is performed on the above mentioned states, for example AND of all states. The logical operation includes at least one of AND, OR, NOT, XOR and XNOR. Models corresponding to different fatigue levels can be obtained by different logical operations, so that the fatigue level of the testee is decided. As a preferred embodiment, the logical operation may be: (State electrocardio[i] & State myoelectric[i])|(State electrocardio[i] & State respiratory[i])|(State myoelectric [i] & State respiratory[i])|(State electrocardio[i] & State myoelectric[i] & State respiratory[i]), wherein "&" represents "AND", "|" represents "OR", and "( )" represents the highest priority.

As an alternative embodiment, each the state function state[i] can be normalized in advance, and then the logical calculation is performed, so that the accuracy of the logical operation model is improved. The normalization may be performed by a normalization model known in the art.

A state logical function of each parameter can be obtained by the state logical operation. The function is a model corresponding to a different fatigue level. The state logical function can be compared and fitted with a plurality of fatigue level models stored in advance in the local storage module. In combination with the body temperature signal parameter, the fatigue level model corresponding to the state logical function can be decided, and the fatigue level is thus determined.

The wearable device for reflecting a fatigue level of a human body provided by the present invention has the following beneficial effects: 1) by directly acquiring an electrocardio signal, the complexity of hardware and software analysis of the device is reduced; 2) by integrating a body temperature sensor into the device, it is convenient to wear, and by providing a multi-parameter portable wearable mode, a user can realize real-time monitoring freely; and, 3) by performing a logical combining operation or normalized logical combining operation by using multiple parameters such as an electrocardio signal, a myoelectric signal, a respiratory signal and a body temperature signal, the scientificity and accuracy of decision are improved.

It should be understood by those skilled in the art that the embodiments of the present disclosure can be provided as methods, apparatuses or computer program products. Therefore, the present application may take the form of full-hardware embodiments, full-software embodiments or embodiments integrating software with hardware. Moreover, the present application may take the form of computer program products that can be implemented on one or more computer-usable storage mediums (including but not limited to magnetic disk storages, CD-ROMs, optical memories or the like) containing computer-usable program codes.

The basic principles, main features and advantages of the present disclosure have been shown and described above. It should be understood by those skilled in the art that the present disclosure is not limited to the foregoing embodiments and the foregoing embodiments and the descriptions in this specification are merely for describing the principle of the present disclosure. Various variation and improvements may be made to the present disclosure without departing from the spirit and scope of the present disclosure, and these variations and improvements shall fall into the protection scope of the present disclosure. The protection scope of the present disclosure is defined by the appended claims and equivalents thereof.

What is claimed is:

1. A method for deciding a fatigue level of a human body, which is applied to a wearable device for reflecting a fatigue level of a human body, the device comprising:
   a physiological signal acquisition module, configured to acquire physiological signals of a testee;
   a signal conditioning module, configured to perform signal conditioning on the physiological signals;
   a parameter extraction module, configured to extract time-domain and frequency-domain parameters in a specific time window; and
   a decision module, configured to decide a fatigue level of the testee;
   a plurality of temperature sensors;
   wherein, an output end of the physiological signal acquisition module is connected to an input end of the signal conditioning module; an output end of the signal conditioning module is connected to an input end of the parameter extraction module; an output end of the parameter extraction module is connected to an input end of the decision module;
   wherein, the method comprises the following steps:
   S1: acquiring physiological signals;
   S2: processing, by a signal conditioning module, a detected data to obtain an electrocardio signal, a respiratory signal, a myoelectric signal and a standard body temperature, respectively; wherein step S2 further comprising,
      S21: performing, by the signal conditioning module, signal conditioning on signals acquired by electrocardio-electrodes, and extracting an electrocardiographic signal, a respiratory signal and a myoelectric signal in the electrocardio-electrode signals by different frequency band filtering; and
      S22: performing temperature compensation on a body temperature signal to obtain a standard body temperature, wherein,
      a number of the temperature sensors equals to n, the standard body temperature is equal to $(i_1T_1+i_2T_2+i_3T_3+ \ldots +i_nT_n)$, n is a number of temperature measurement points, $i_1$ to $i_n$ are parameters corresponding to the temperature measurement points, and $i_1+i_2+i_3+ \ldots +i_n+1$, before detection, detection positions of a shell temperature are systematically set, a weighed value of the body temperatures at different parts is obtained by reading a corresponding data table in a local storage module through the compensation module, and a combination of a set of parameters is further obtained through the weighted value;
   S3: further extracting, by a parameter extraction module, corresponding feature values according to the electrocardio signal, the respiratory signal, the myoelectric signal and the standard body temperature obtained in the step S2; and
   S4: setting, by a decision module and according to a change trend of the body temperature, an upper threshold limit and a lower threshold limit for the electrocardio signal, the respiratory signal and the myoelectric signal, to decide whether it is normal or abnormal, and performing logical combining to obtain a fatigue level model for further deciding the fatigue level.

2. The method for deciding a fatigue level of a human body according to claim 1, wherein, the step S3 further comprises the following steps:
   S31: extracting, from the electrocardio signal, feature values of heart rate variability;
   S32: extracting, from the respiratory signal, feature values comprising a maximum value and a minimum value of the respiratory frequency;
   S33: extracting, from the myoelectric signal, feature values comprising a median frequency and an average frequency; and
   S34: extracting, from the standard body temperature signal, feature values comprising a maximum value, a minimum value, a mean value and a standard deviation of the body temperature.

3. The method for deciding a fatigue level of a human body according to claim 1, wherein, the physiological signal acquisition module comprises electrocardio-electrodes and a body temperature acquisition module, which are configured to acquire electrocardio-electrode physiological signals and body temperature physiological signals, respectively.

4. The method for deciding a fatigue level of a human body according to claim 1, wherein the signal conditioning module comprises a filtering circuit.

5. The method for deciding a fatigue level of a human body according to claim 1, wherein, the electrocardio-electrodes comprise two or more electrocardio-electrodes.

6. The method for deciding a fatigue level of a human body according to claim 1, wherein, the device further comprises a wireless communication module, a local storage module, a display and feedback module and a power supply module.

\* \* \* \* \*